United States Patent [19]

Schaus

[11] Patent Number: 4,540,787

[45] Date of Patent: Sep. 10, 1985

[54] METHOD OF PREPARING TRANS-D1-1-ALKYL-6-OXODECAHYDROQUINOLINES

[75] Inventor: John M. Schaus, Indianapolis, Ind.

[73] Assignee: Eli Lilly and Company, Indianapolis, Ind.

[21] Appl. No.: 521,863

[22] Filed: Aug. 10, 1983

Related U.S. Application Data

[63] Continuation-in-part of Ser. No. 384,817, Jun. 3, 1982, abandoned.

[51] Int. Cl.[3] .......................................... C07D 215/20
[52] U.S. Cl. ................................................. 546/164
[58] Field of Search ........................................ 546/164

[56] References Cited

U.S. PATENT DOCUMENTS 4,198,415  4/1980  Kornfeld et al. .................... 424/258
4,235,909  11/1980  Bach et al. ........................... 424/258

OTHER PUBLICATIONS

Tsuruta et al., *Nature*, 292, 463 (1981).
Honel et al., *J.C.S. Perkin I*, 1980, 1933.
Okieman et al., *J. Roy. Neth. Chem. Soc.*, 99, 353 (1980).
Leonard et al., *J. Org. Chem.*, 27, 4027 (1962).
Birch et al., *J.C.S.*, 637 (1971).
Birch and Dyke, *Aust. J. Chem.*, 31, 1625 (1978).
Borch et al., *J.A.C.S*, 93, 2897 (1971).

*Primary Examiner*—Glennon H. Hollrah
*Assistant Examiner*—D. B. Springer
*Attorney, Agent, or Firm*—James L. Rowe; Arthur R. Whale

[57] ABSTRACT

A process for preparing 1-alkyl-6-oxodecahydroquinolines in 5 steps—a quaternization, hydrogenation, two organometallic reductions and hydrolysis of the thus formed enol ether—from 6-alkyloxyquinoline and intermediates useful therein.

11 Claims, No Drawings

METHOD OF PREPARING TRANS-Dl-1-ALKYL-6-OXODECAHYDROQUINO-LINES

CROSS-REFERENCE

This application is a continuation-in-part of my co-pending application Ser. No. 384,817 filed June 3, 1982, abandoned.

BACKGROUND OF THE INVENTION

U.S. Pat. No. 4,198,415 discloses a group of octahydropyrazolo[3,4-g]quinolines useful as prolactin inhibitors and in the treatment of Parkinsonism. The compounds disclosed therein are said to have D-2 dopamine agonist (dopaminergic) activity, according to Tsuruta et al Nature, 292, 463 (1981). One of the more active drugs disclosed carries an n-propyl group on the quinoline nitrogen.

A key intermediate in the preparation of these octahydropyrazolo[3,4-g]quinolines is a transdl-1-alkyl-6-oxodecahydroquinoline, one of whose stereoisomers (the 4aα, 8aβ compound) is disclosed in VII of column 5 of U.S. Pat. No. 4,198,415. The same intermediate is used to prepare a related group of compounds, the 4,4a,5,6,7,8,8a,9-octahydro-2H-pyrrolo[3,4-g]quinolines of U.S. Pat. No. 4,235,909, --see compound VII, column 3, lines 50-60 (the compound represented by VII is a typographical error since it lacks the keto group at 6. This error has been noted in the file of U.S. Pat. No. 4,235,909, since it is clear from the context that VII should have a ketone group at C-6). The octahydro-2H-pyrrolo[3,4-g]quinolines are similar in activity to the octahydro-1H(and 2H)-pyrazolo[3,4-g]quinolines in that the compounds are inhibitors of prolactin secretion and also show activity in experimental models of Parkinson's disease.

U.S. Pat. No. 4,198,415 also discloses the reduction of a mixture of double bond isomers, dl-1-alkyl-6-hydroxy-1,2,3,4,5,6,7,8-octahydroquinoline and dl-1-alkyl-6-hydroxy-1,2,3,4,4a,5,6,7-octahydro quinoline with NaBH₃CN to yield trans-dl-1-alkyl-6-hydroxydecahydroquinoline.

The hydrogenation of a 6-methoxyquinoline is shown in Honel et al, J.C.S. Perkin I, 1980, 1933. Hydrogenation over platinum in neutral or weakly acidic media results in hydrogenation of the pyridine ring, whereas hydrogenation in acidic (12N HCl or CF₃COOH) results in hydrogenation of the benzene ring. Birch reduction of a 6-methoxy-1-benzyl 1,2,3,4-tetrahydroisoquinoline is shown in Okieman et al, J. Roy. Neth. Chem. Soc., 99 353 (1980). Reduction of 1-methyl-1,2,3,4-tetrahydroquinoline to a mixture of 1-methyloctahydroquinolines is shown in Leonard et al, J. Org. Chem. 27, 4027 (1962). Lithium and isopropylamine was the reducing agent. In this instance, Birch reduction introduced 4 hydrogens into the benzene ring. Birch et al J.C.S., 637 (1971) reduced a series of N,N-dimethylanilines with Li in liquid ammonia to produce conjugated cyclohexadiene amines. In general, m and p-anisidines (m and p-methoxy dimethyl anilines) gave the conjugated cyclohexadiene on Birch reduction but the ortho derivative gave the nonconjugated (page 638, formula 3) diene. Reduction of N-(p-methoxyphenyl)-morpholine, according to Birch and Dyke, Aust. J. Chem., 31, 1625 (1978) also gave the unconjugated diene on reduction with Li and liquid NH₃. Both of these reductions involved exocyclic amine functions attached to a benzene ring system containing also a p-methoxy group. Reductions of endocyclic amines, as in an N-alkyl 6-methoxytetrahydroquinoline, are not recorded.

Finally Borch et al, J.A.C.S., 93, 2897 (1971) discuss the reduction of enamines with NaBH₃CN. No instance of a reduction of an endocyclic double bond of an enamine in which the ring contains a second double bond, has been found.

The method of synthesizing trans-dl-1-alkyl-6-oxodecahydroquinolines, as disclosed in U.S. Pat. Nos. 4,198,415 and 4,235,909 patents, while operative, involves five steps from a commercially available starting material. Furthermore, yields are not as high as desirable for a commercial process.

It is an object of this invention to provide an improved method of preparing trans-dl-1-alkyl-6-oxodecahydroquinolines which is easier to carry out and which gives higher yields than the process previously used.

SUMMARY OF THE INVENTION

In fulfillment of the above and other objects, this invention provides an improved method of preparing trans-dl-1-alkyl-6-oxo-1,2,3,4,4a,5,6,7,8,8a-decahydroquinolines, a racemic mixture. This racemic mixture is comprised of equal amounts of two stereoisomers represented by formulas Ia and Ib below. The isomer of formula Ia is named as a 1-alkyl-6-oxo-1,2,3,4,4aβ,5,6,7,8,8aα-decahydroquinoline and the isomer of formula Ib is named as a trans-dl-1-alkyl-6-oxo1,2,3,4,4aα,5,6,7,8,8aβ-decahydroquinoline.

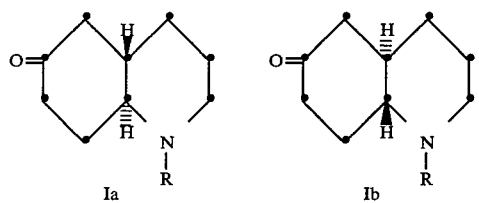

Racemic Mixture

In the above structures, R is lower alkyl such as methyl, ethyl and n-propyl.

My novel method of preparing this racemate is described, in its broader aspects, in the reaction scheme which follows:

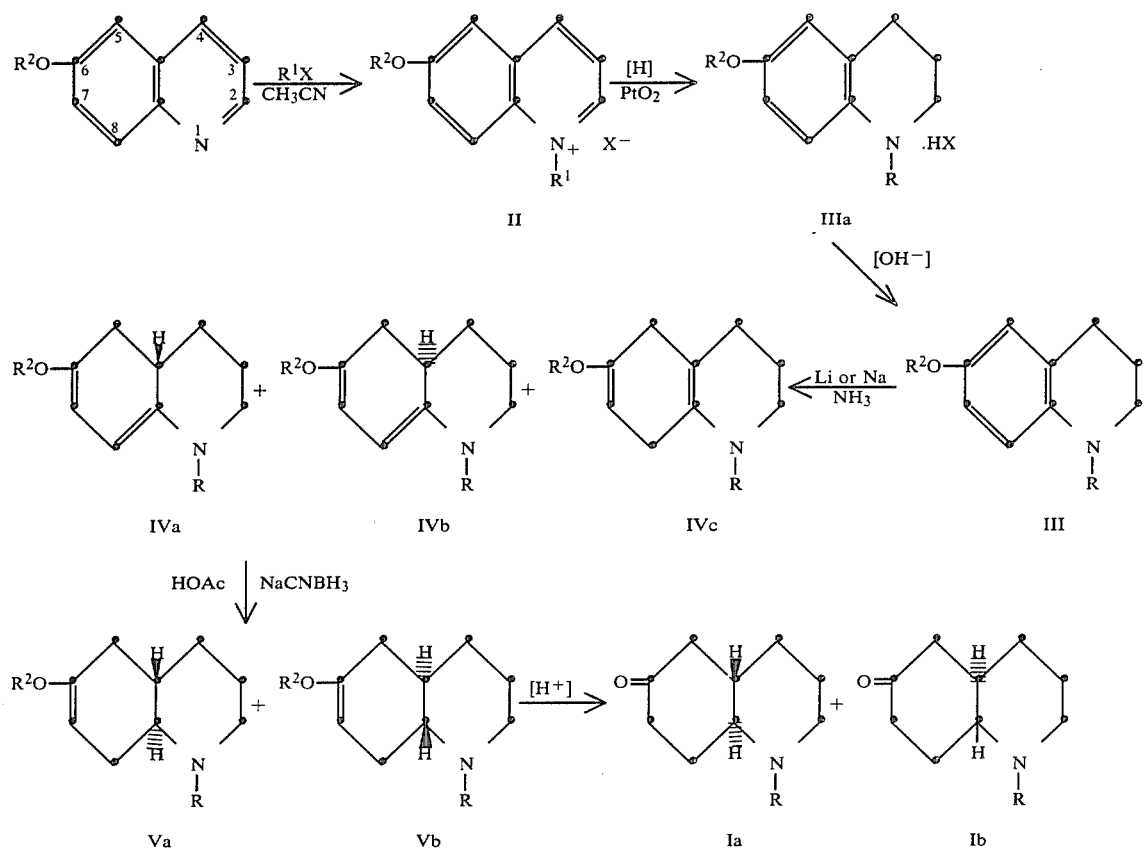

wherein R and R² are separately C₁₋₃ alkyl, X is a halogen or a pseudohalogen and R¹ is R or allyl.

According to the above reaction scheme a 6-alkoxyquinoline such as 6-methoxyquinoline (available commercially), is quarternized with an alkyl or allyl halide or pseudo halide (R¹X), preferably an alkyl iodide (RI), in an inert solvent such as acetonitrile. The term "pseudo halide" here refers to such nucleophilic (leaving) groups as mesyloxy or tosyloxy which behave chemically in S_N2 reactions like a halide group. The quaternization reaction is carried out conveniently at the boiling point of the solvent employed. The quaternary salt (II) is a crystalline material.

In the second step of the synthetic procedure, this salt is hydrogenated under pressure using a noble metal catalyst such as platinum (supplied as PtO₂), palladium, ruthenium or rhodium. This hydrogenation is preferably carried out in an acidic medium such as glacial acetic acid and at elevated temperatures; i.e., in the range 60°–100° C. Both low and high pressure reaction conditions are operative; i.e., pressures varying from 50–60 psi for low pressure hydrogenation to up to 1000 psi for high pressure hydrogenation are operative. For example, about ten hours are required to reduce one-half mole of II to 1-alkyl-6-methoxy-1,2,3,4-tetrahydroquinoline, as the hydrogen iodide salt (IIIa) at 1000 psi with a PtO₂ catalyst in glacial acetic acid.

The free base (III) is prepared from the salt by treatment of an aqueous solution of the salt with base followed by extraction of the base-insoluble tetrahydroquinoline into a water immiscible solvent.

An alternate method of preparing III consists of reduction of 6-methoxyquinoline at low pressure over a noble metal catalyst such as PtO₂ in an inert solvent and then alkylating 6-methoxy-1,2,3,4-tetrahydroquinoline as with an aldehyde (HCHO, CH₃CHO, C₂H₅CHO) under reducing conditions such as low pressure hydrogenation over a noble metal catalyst such as Pd-on-C in an inert solvent. Useful inert solvents include the lower alkanols, THF, aromatic hydrocarbons and the like.

In a second reduction step, the tetrahydroquinoline is reduced under Birch reduction conditions, using an alkali metal, such as sodium or lithium, dissolved in liquid ammonia. The quinoline is customarily added as a solution in THF to the solution of the alkali metal in liquid NH₃. After the reduction mixture is stirred at liquid ammonia temperatures for a suitable period of time, anhydrous ethanol is added until the blue solution color characteristic of liquid ammonia solution of alkali metals is discharged. The reaction mixture is then allowed to warm to room temperature as the NH₃ evaporates. The residual THF solution contains a mixture of hexahydroquinolines represented by IVa (1-alkyl-6-alkoxy-1,2,3,4,4aβ,5-hexahydroquinoline), IVb (1-alkyl-6-alkoxy-1,2,3,4,4aα,5-hexahydroquinoline) and IVc (1-alkyl-6-methoxy-1,2,3,4,5,8-hexahydroquinoline). This mixture of hexahydroquinoline isomers is then stereoselectively reduced using sodium cyanoborohydride or sodium borohydride. A solvent such as THF is employed in this reduction and a small quantity of glacial acetic acid is also added. The reduction is conveniently carried out at room temperature. The borohydride or cyanoborohydride reduction of IVa and IVb to yield an enol ether and the enol ether intermediates produced thereby form a second embodiment of this invention.

The product of the reduction is a racemate, represented by Va and Vb above. Va is named as a 1-alkyl-6-alkoxy-1,2,3,4,4aβ,5,8,8aα-octahydroquinoline and Vb is named as a 1-alkyl-6-alkoxy-1,2,3,4,4aα,5,8,8aβ-octahydroquinoline. Treatment of this racemate with aqueous acid, preferably HCl, yields a racemic mixture of Ia and Ib, trans-dl-1-alkyl-6-oxodecahydroquinolines.

Preparation of the above compounds is illustrated by the following specific Examples.

EXAMPLE 1

Preparation of 1-n-Propyl-6-methoxyquinolinium iodide.

Four hundred grams of 6-methoxyquinoline were dissolved in 2.5 l. of acetonitrile containing 854.4 g. of n-propyl iodide. The resulting solution was heated to reflux for about 18 hours under a nitrogen blanket. The reaction mixture was cooled and the solvent removed by evaporation in vacuo. The residue was dissolved in acetone and ether was added to the point of incipient precipitation. Crystals were produced by scratching. Crystalline 1-n-propyl-6-methoxyquinolinium iodide thus prepared was isolated by filtration; weight=547.2 g.; melting point=111°-115° C. $R_f$(4:1 chloroform:methanol, silica)=0.58. An additional 136.2 g. of desired product were obtained from the filtrate. NMR was compatible with the proposed structure.

EXAMPLE 2

Preparation of 1-n-Propyl-6-methoxy-1,2,3,4-tetrahydroquinoline 1-n-Propyl-6-methoxyquinolinium iodide was hydrogenated to yield 1-n-propyl-6-methoxy-1,2,3,4-tetrahydroquinoline. In a typical run, 163 g. of the quarternary salt were dissolved in 1917 ml. of glacial acetic acid to which were added 20 g. of platinium oxide. Hydrogenation was carried out at 1000 psi at a temperature of about 100° C. After about ten hours, the theoretical amount of hydrogen had been absorbed. The hydrogenation mixture was then filtered to remove the catalyst and the solvent then removed from the filtrate by evaporation in vacuo. The resulting residue was dissolved in water and the aqueous solution made basic by the addition of saturated aqueous sodium bicarbonate. The aqueous layer was extracted with ether. The ether extracts containing 1-n-propyl-6-methoxy-1,2,3,4-tetrahydroquinoline formed in the above reaction were washed with water and then dried. The ether was removed by evaporation in vacuo. Ninety-two grams of 1-n-propyl-6-methoxy-1,2,3,4-tetrahydroquinoline were obtained; yield=90.6%.

The above hydrogenation can also be carried at a low pressure such as 60 psi. In addition, in place of PtO2, Pd-on-C can also be used with equal or superior results.

Alternatively, an alkyl halide such as allyl bromide can be used to quaternize the 6-methoxyquinoline since hydrogenation of the N-allyl-6-methoxyquinolinium bromide with a noble metal catalyst such as PtO2, Pd-on-C, Rb on Al2O3 etc. will ultimately yield the identical 1-n-propyl-6-methoxy-1,2,3,4-tetrahydroquinoline.

EXAMPLE 3

Preparation of 1-n-Propyl-6-methoxy-1,2,3,4,5,8-hexahydroquinoline, 1-n-Propyl-6-methoxy-1,2,3,4,4aα,5-hexahydroquinoline and 1-n-Propyl-6-methoxy-1,2,3,4,4aβ,5-hexahydroquinoline Three liters of ammonia were dried over sodium metal for about one hour. 800 ml. of ammonia thus dried were then distilled into a 3 l. three-neck flask equipped with gas inlet tube, condenser with drying tube attached and addition funnel. The ammonia was stirred with a magnetic stirrer. A solution containing 40 g. of 1-n-propyl-6-methoxy-1,2,3,4-tetrahydroisoquinoline in 200 ml. of THF (dry, distilled) were added. Ten g. of lithium metal were cut into chunks of about 1 cc size and these chunks were added in a single batch to the liquid ammonia-tetrahydroquinoline-THF solution. The reaction mixture was stirred for about 20 minutes. Anhydrous ethanol (about 160 ml.) was added in dropwise fashion over a 15 minute period. The resulting mixture was allowed to stir overnight under a nitrogen atmosphere without external cooling. During this time, the ammonia evaporated. Four-hundred ml. of water were then added. The aqueous mixture was extracted with three 200 ml. portions of methylenedichloride. The methylenedichloride layers were combined and the combined layers washed with 250 ml. of saturated aqueous sodium chloride. The methylenedichloride layers were then dried and the solvent removed by evaporation in vacuo. The mixture of 1-n-propyl-6-methoxy-1,2,3,4,5,8-hexahydroquinoline, 1-n-propyl-6-methoxy-1,2,3,4,4aα,5-hexahydroquinoline and 1-n-propyl-6-methoxy-1,2,3,4,4aβ,5-hexahydroquinoline thus produced distilled in the range 84°-120° C. at a pressure of 0.03 Torr; yield=32.6 g. (80.5%).

EXAMPLE 4

Preparation of trans-dl-1-n-Propyl-6-methoxy-1,2,3,4,4a,5,8,8a-octahydroquinoline A solution was prepared containing 4.4 g. of sodium cyanoborohydride in 250 ml. of dried, distilled THF. 14.8 g. of a mixture of 1-n-propyl-6-methoxy-1,2,3,4,5,8-hexahydroquinoline, 1-n-propyl-6-methoxy-1,2,3,4,4aα,5-hexahydroquinoline and 1-n-propyl-6-methoxy-1,2,3,4,4aβ,5-hexahydroquinoline mixture in 100 ml. of THF were then added, followed by 1.7 ml. of glacial acetic acid. The reaction mixture was stirred at ambient temperature for about 1.25 hours, at which time another 1.7 ml. of glacial acetic acid were added. Stirring was continued for an additional 30 minutes. The entire reaction mixture was then poured into about 300 ml. of water. The aqueous mixture was extracted three times with 200 ml. of portions of methylenedichloride. The organic layers were combined, the combined layers were washed once with an equal volume of water and were then dried. The solvent was removed by evaporation in vacuo and the residual yellow viscous oil was distilled. Trans-dl-1-n-propyl-6-methoxy-1,2,3,4,4a,5,8-,8a-octahydroquinoline thus prepared distilled in the range 95°-140° C. at 0.2 Torr. or 70°-95° C. at 0.15 Torr. The two distillates were combined, giving a total weight of 10 g. (66% yield). The combined distillates were stored under nitrogen.

EXAMPLE 5

Alternate preparation of trans-dl-1-n-Propyl-6-methoxy-1,2,3,4,4a,5,8,8a-octahydroquinoline A solution of 10 g. of a mixture of 1-n-propyl-6-methoxy-1,2,3,4,5,8-hexahydroquinoline, 1-n-propyl-6-methoxy-1,2,3,4,4aR,5-hexahydroquinoline, and 1-n-propyl-6-methoxy-1,2,3,4,4aS,5-hexahydroquinoline in 140 ml. of ethanol was prepared. 2.5 ml. of glacial acetic acid were added. A solution of 1.32 g. of sodium borohydride in ethanol was next added portionwise to the first solution and the consequent reaction mixture was cooled and stirred under nitrogen for about 16 hours. Trans-dl-1-n-propyl-6-methoxy-1,2,3,4,4a,5,8,8a-octahydroquinoline thus prepared was isolated according to the procedure of Example 1; yield=82%.

The above procedure was repeated using 140 ml. of isopropanol in place of 140 ml. of ethanol, yield=52%; using 140 ml. of methanol, yield=92%; using 40 ml. of ethanol to dissolve the NaBH₄ and 100 ml. of methanol as a solvent, yield=98%.

A run using 10 g. of starting material in 100 ml. of methanol, 1.07 g. of NaBH₄ in 40 ml. of ethanol and 2.8 g. of glacial acetic acid gave a 99% yield of the desired 1-n-propyl-6-methoxyoctahydroquinoline.

EXAMPLE 6

Preparation of trans-dl-1-n-Propyl-6-oxo-1,2,3,4,4a,5,6,7,8,8a-decahydroquinoline A solution was prepared from 3.1 g. of trans-dl-1-n-propyl-6-methoxy-1,2,3,4,4a,5,8,8a-octahydroquinoline in 25 ml. of THF. Four ml. of 10% aqueous sulfuric acid were added. The resulting two-phase mixture was heated at refluxing temperature for about 17 hours after which time it was poured into dilute aqueous sodium hydroxide. The alkaline aqueous mixture was extracted with methylenedichloride. The methylenedichloride extract was dried and the solvent removed in vacuo. A residual oil weighing about 2.8 g. comprising trans-dl-1-n-propyl-6-oxodecahydroquinoline distilled in the range 63°–87° C. at 0.1 Torr. TLC indicated that the combined fractions contained in excess of 90% trans-dl-1-n-propyl-6-oxodecahydroquinoline.

Alternately, 5.0 g. of trans-dl-1-n-propyl-6-methoxy-1,2,3,4,4a,5,8,8a-octahydroquinoline were dissolved in 50 ml. of THF. Twenty-five ml. of 1N aqueous hydrochloric acid were added and the mixture stirred for one-half hour under a nitrogen atmosphere. The reaction mixture was then made basic with 14N aqueous ammonium hydroxide and the alkaline mixture extracted three times with methylenedichloride. The organic extracts were combined, dried and the solvent removed in vacuo. 4.8 g. of an orange transparent oil remained as a residue. TLC indicated a single spot at $R_f$=0.67 with slight leading and trailing spots as impurities. Distillation yielded trans-dl-1-n-propyl-6-oxodecahydroquinoline boiling at 77°–87° C. at 0.025 Torr. total yield=4.39 g. (94.1%).

EXAMPLE 7

Alternate preparation of 1-n-propyl-6-methoxy-1,2,3,4-tetrahydroquinoline

A solution of 218.5 g. of 6-methoxyquinoline in 1750 ml of methanol was hydrogenated at 60 psi over 30 g. of platinum dioxide at 50° overnight. The reaction was filtered and the filtrate concentrated to give an oil. The oil was distilled to give 148.6 g. of 6-methoxy-1,2,3,4-tetrahydroquinoline (66% yield) boiling in the range 123°–125° C. at 8 Torr.

A solution of 148.6 g. of 6-methoxy-1,2,3,4-tetrahydroquinoline and 58 g. of propionaldehyde in 275 ml. of ethanol was hydrogenated at 60 psi over 15 g. of 15% palladium on carbon at room temperature for 2 hours and then at 50° C. overnight. The catalyst was removed by filtration and the filtrate concentrated to give a brown oil which was distilled to give 100.5 g. of 6-methoxy-1-n-propyl-1,2,3,4-tetrahydroquinoline (54% yield) as an oil boiling in the range 115°–128° C. at 0.02 Torr.

As previously stated, the products of the synthetic methods of this invention, the trans-dl-1-alkyl-6-oxodecahydroquinolines (Ia and Ib), can be reacted with dimethylformamide dimethylacetal to yield a trans-dl-1-alkyl-6-oxo-7-dimethylaminomethylene decahydroquinoline. Reaction of this intermediate with potassium glycinate followed by treatment with acetic anhydride yields a trans-dl-2-acetyl-5-alkyl-4,4a,5,6,7,8,8a,9-octahydro-2H-pyrrolo[3,4-g]quinoline. Alkaline hydrolysis of the acetyl derivative yields trans-dl-5-alkyl-4,4a,5,6,7,8,8a,9-octahydropyrrolo[3,4-g]quinoline, a dopamine agonist useful in treating Parkinsonism or excessive prolactin secretion (see U.S. Pat. No. 4,235,909). Alternatively, the compound reacts with hydrazine to yield a tautomeric mixture consisting of trans dl-5-alkyl-4,4a,5,6,7,8,8a,9-octahydro-1H-pyrazolo[3,4-g]quinoline and the corresponding 2H compound, useful also as dopamine agonists. (see U.S. Pat. No. 4,198,415).

I claim:

1. The synthetic method which comprises the steps of:

A. quaternizing a 6-alkyloxyquinoline with a $C_{1-3}$ alkyl halide or pseudo halide or with an allyl halide or pseudo halide in an inert mutual solvent to yield a quaternary salt of the formula

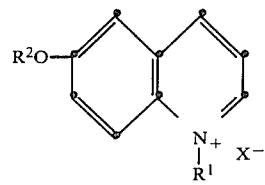

wherein $R^2$ is $C_{1-3}$ alkyl, $R^1$ is $R^2$ or allyl and X is a halogen or pseudo halogen;

B. hydrogenating said quaternary salt in an inert mutual solvent under pressure using a noble metal catalyst to yield a tetrahydroquinoline salt of the formula

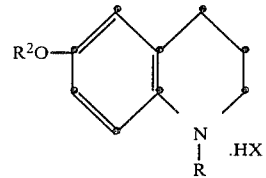

wherein R and $R^2$ are separately $C_{1-3}$ alkyl and X has its previously assigned meaning;

C. converting said HX salt to the corresponding free base with aqueous alkali;

D. reducing said free base with an alkali metal in liquid ammonia, optionally in the presence of a second mutual inert solvent, to yield a mixture of N-alkyl hexahydroquinolines of the formulas

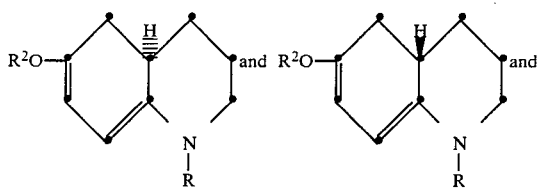

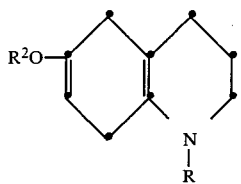

wherein R and R² have their previous meaning;

E. reducing said hexahydroquinoline mixture with a borohydride in glacial acetic acid and a mutual inert solvent to yield a racemic mixture of octahydroquinolines of the formula

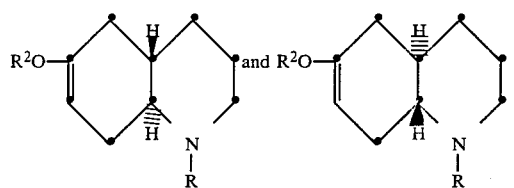

F. treating said racemic mixture with acid in an inert mutual solvent to form a racemic mixture of 6-oxodecahydroquinolines of the formula

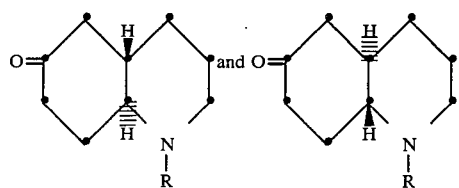

G. and then isolating said racemate, or an acid addition salt thereof, in substantially pure form.

2. A process according to claim 1 in which R² is methyl.

3. A process according to claim 1 in which R¹ and R are n-propyl.

4. A process according to claim 1 in which the noble metal catalyst of Step B is PtO₂ or Pd-on-C.

5. A process according to claim 4 in which the hydrogenation is carried out at about 50–1000 psi and about 60°–100° C.

6. A process according to claim 1 in which the second solvent for Step C is acetonitrile.

7. A process according to claim 1 in which 6-methoxyquinoline is quaternized with n-propyl iodide; the quaternary salt is hydrogenated using a noble metal catalyst to produce 1-n-propyl-6-methoxy-1,2,3,4-tetrahydroquinoline hydriodide; the hydriodide salt is converted to the corresponding free base by treatment with aqueous alkali; the 1,2,3,4-tetrahydroquinoline free base is reduced with lithium in liquid ammonia and 8. In the process of converting a 6-C$_{1-3}$ alkoxyquinoline to a trans-dl-1-C$_{1-3}$ alkyl-6-oxodecahydroquinoline according to claim 1, the process step which comprises the step of reducing a 1-C$_{1-3}$alkyl-6-C$_{1-3}$alkyloxy-1,2,3,4-tetrahydroquinoline to an isomeric mixture of a 1-C$_{1-3}$alkyl-6-C$_{1-3}$alkyloxy-1,2,3,4,4aα,5-hexahydroquinoline, a 1-C$_{1-3}$alkyl-6-C$_{1-3}$alkyloxy-1,2,3,4,4aβ,5-hexahydroquinoline and a 1-C$_{1-3}$alkyl-6-C$_{1-3}$alkyloxy-1,2,3,4,5,8-hexahydroquinoline with an alkali metal in liquid ammonia.

9. In the process of converting a 6-C$_{1-3}$ alkyloxyquinoline to a trans-dl-1-C$_{1-3}$ alkyl-6-oxodecahydroquinoline according to claim 1, the process step which comprises reducing an isomeric mixture of a 1-C$_{1-3}$alkyl-6-C$_{1-3}$alkyloxy-1,2,3,4,4aα,5-hexahydroquinoline, 1-C$_{1-3}$alkyl-6-C$_{1-3}$alkyloxy-1,2,3,4,4aβ,5-hexahydroquinoline and 1-C$_{1-3}$alkyl-6-C$_{1-3}$alkyloxy-1,2,3,4,5,8-hexahydroquinoline to trans-dl-1,2,3,4,4a,5,8,8a-octahydroquinoline with a borohydride optionally in the presence of glacial acetic acid plus an inert mutual solvent.

10. A process according to claim 9 in which an isomeric mixture of 1-n-propyl-6-methoxy-1,2,3,4,4aα,5-hexahydroquinoline, 1-n-propyl-6-methoxy-1,2,3,4,4aβ,5-hexahydroquinoline and 1-n-propyl-6-methoxy-1,2,3,4,5,8-hexahydroquinoline is reduced to yield trans-dl-1-n-propyl-6-methoxy-1,2,3,4,4a,5,8,8a-octahydroquinoline.

11. The synthetic method which comprises the steps of:

A. hydrogenating 6-alkyloxyquinoline over a noble metal catalyst in an inert mutual solvent to yield a compound of the formula

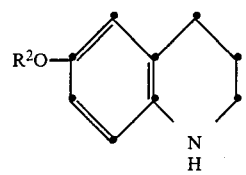

wherein R² is C$_{1-3}$ alkyl;

B. alkylating said tetrahydroquinoline with an aldehyde R³CHO wherein R³ is H, CH₃ or C₂H₅ in an inert mutual solvent under pressure using a noble metal catalyst to yield a tetrahydroquinoline of the formula

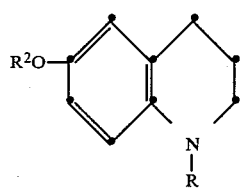

wherein R and R² are separately C$_{1-3}$ alkyl;

C. reducing said free base with an alkali metal in liquid ammonia, optionally in the presence of a second mutual inert solvent, to yield a mixture of N-alkyl hexahydroquinolines of the formulas

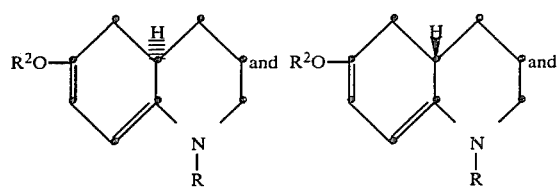 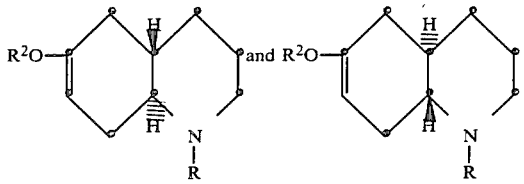

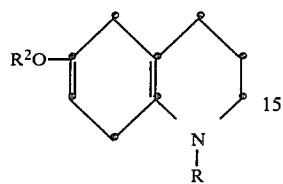

wherein R and R² have their previous meaning;

D. reducing said hexahydroquinoline mixture with a borohydride in glacial acetic acid and a mutual inert solvent to yield a racemic mixture of octahydroquinolines of the formula

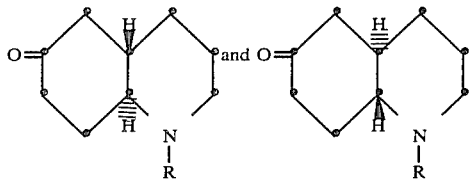

E. treating said racemic mixture with acid in an inert mutual solvent to form a racemic mixture of 6-oxodecahydroquinolines of the formula F. and then isolating said racemate, or an acid addition salt thereof, in substantially pure form.

* * * * *